United States Patent
Rolez et al.

(10) Patent No.: US 11,261,150 B2
(45) Date of Patent: *Mar. 1, 2022

(54) METHOD FOR PURIFYING (METH)ACRYLIC ESTERS

(71) Applicant: Arkema France, Colombes (FR)

(72) Inventors: Eloi Rolez, Metz (FR); Serge Tretjak, Roulhing (FR)

(73) Assignee: Arkema France, Colombes (FR)

( * ) Notice: Subject to any disclaimer, the term of this patent is extended or adjusted under 35 U.S.C. 154(b) by 130 days.

This patent is subject to a terminal disclaimer.

(21) Appl. No.: 16/616,528

(22) PCT Filed: Jul. 3, 2018

(86) PCT No.: PCT/FR2018/051645
§ 371 (c)(1),
(2) Date: Nov. 25, 2019

(87) PCT Pub. No.: WO2019/020889
PCT Pub. Date: Jan. 31, 2019

(65) Prior Publication Data
US 2021/0300857 A1 Sep. 30, 2021

(30) Foreign Application Priority Data
Jul. 25, 2017 (FR) ...................... 1757038

(51) Int. Cl.
*C07C 67/54* (2006.01)
*C07C 67/02* (2006.01)

(52) U.S. Cl.
CPC .............. *C07C 67/54* (2013.01); *C07C 67/02* (2013.01)

(58) Field of Classification Search
CPC ........ C07C 67/54; C07C 67/02; C07C 213/10; C07C 219/08; C07C 213/06; C07C 69/54; C07C 67/03; B01D 3/141; Y02P 20/584
See application file for complete search history.

(56) References Cited

U.S. PATENT DOCUMENTS

| | | | |
|---|---|---|---|
| 6,437,173 B1 | 8/2002 | Hurtel et al. | |
| 7,268,251 B2 | 9/2007 | Geisendoerfer et al. | |
| 7,294,240 B2 | 11/2007 | Geisendoerfer et al. | |
| 9,018,410 B2 | 4/2015 | Riondel et al. | |
| 10,000,439 B2 | 6/2018 | Riondel et al. | |
| 2013/0245309 A1 | 9/2013 | Chalfant et al. | |
| 2013/0284586 A1* | 10/2013 | Lee ...................... | B01D 3/141 203/99 |
| 2016/0158667 A1 | 6/2016 | Lee et al. | |

FOREIGN PATENT DOCUMENTS

| | | | |
|---|---|---|---|
| CN | 1054117 | * | 7/2000 |
| CN | 106861353 A | | 6/2017 |
| JP | 2005 239564 | * | 8/2005 |
| JP | 2005 239564 | | 9/2005 |

OTHER PUBLICATIONS

JP 2005 239564 translated (Year: 2005).*
Ramapriya et al. (Thermal Coupling Links to Liquid-Only Transfer Streams: An Enumeration Method for New FTC Dividing Wall Columns, AIChE Journal, vol. 62, No. 4, pp. 1200-1211, Published Apr. 2016) (Year: 2016).*
CN1054117 translated (Year: 2000).*
Asprion N, et al, "Dividing wall columns: Fundamentals and recent advances", Chem Engineering and Processing, Elsevier Sequoia, vol. 49, No. 2, Jan. 25, 2010 (pp. 139-146).
Dejanovic, I, et al, "Dividing wall column—A breakthrough towards sustainable distilling", Chem Engineering and Processing, Elsevier Sequoia, vol. 49, No. 6, Apr. 12, 2010 (pp. 559-580).

* cited by examiner

*Primary Examiner* — Jafar F Parsa
*Assistant Examiner* — Blaine G Doletski
(74) *Attorney, Agent, or Firm* — Lynn B. Morreale

(57) ABSTRACT

The invention relates to the production of (meth)acrylic esters according to a continuous process by transesterification, and in particular to the purification of a crude reaction mixture comprising a $C_4$-$C_{12}$ (meth)acrylic ester using a divided wall column employed in a particular configuration. This configuration results in a simplification of the purification process with a reduced energy consumption and a minimized content of impurities present in the purified (meth)acrylic ester. The invention also relates to a process for the production of $C_4$-$C_{12}$ (meth)acrylic ester comprising this recovery/purification process.

12 Claims, 1 Drawing Sheet

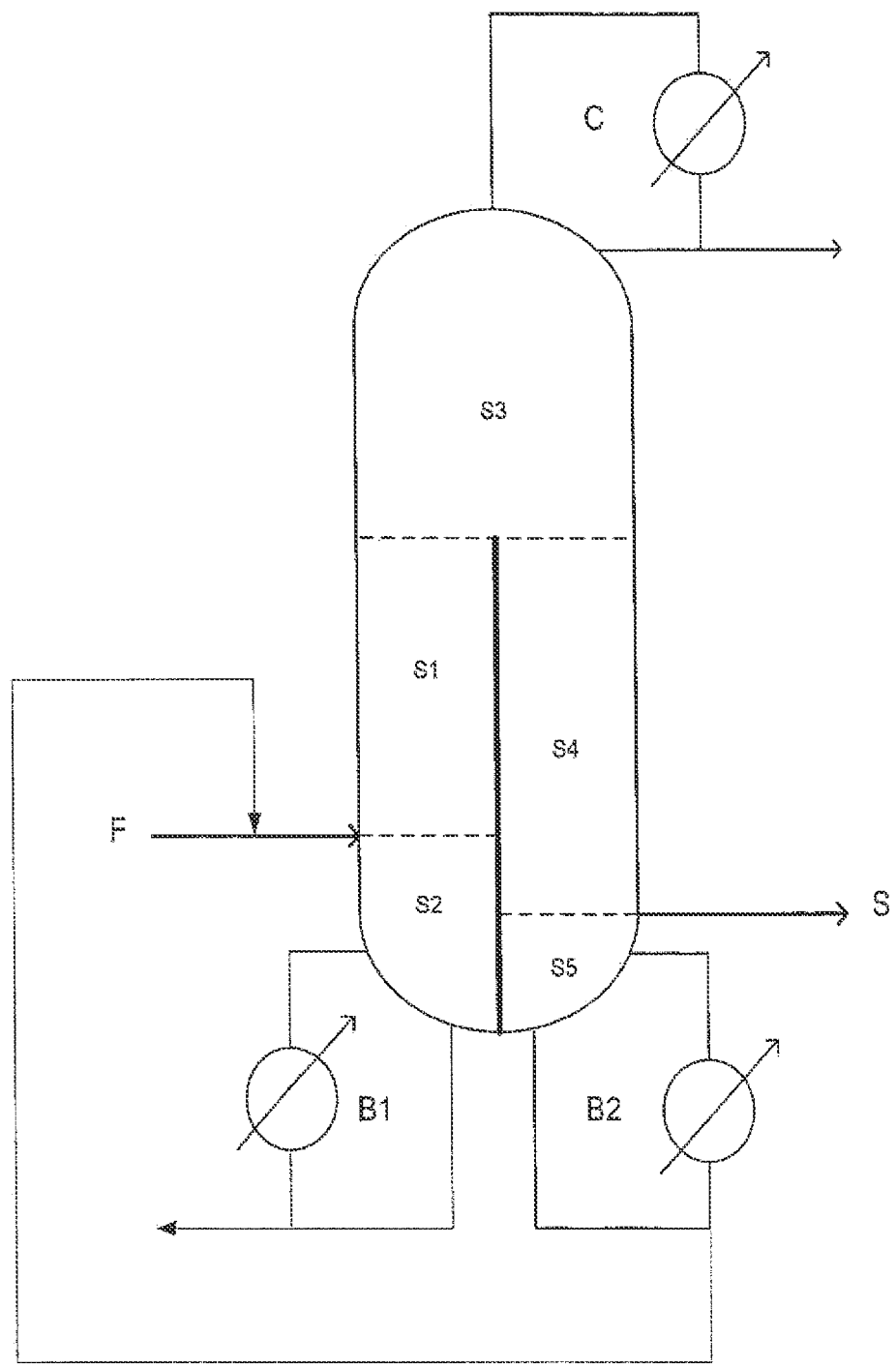

METHOD FOR PURIFYING (METH)ACRYLIC ESTERS

CROSS-REFERENCE TO RELATED APPLICATIONS

This application is a national stage application under 35 U.S.C. § 371 of PCT/FR2018/051645, filed Jul. 3, 2018 which claims benefit to application FR17.57038, filed Jul. 25, 2017.

TECHNICAL FIELD

The present invention relates to the production of (meth)acrylic esters according to a continuous process by transesterification, and in particular to the purification of a crude reaction mixture comprising a $C_4$-$C_{12}$ (meth)acrylic ester using a divided wall column employed in a particular configuration.

This configuration results in a simplification of the purification process with a reduced energy consumption and a minimized content of impurities present in the purified (meth)acrylic ester.

The invention also relates to a process for the production of $C_4$-$C_{12}$ (meth)acrylic ester comprising this recovery/purification process

Technical Background and Technical Problem $C_4$-$C_{12}$ (meth)acrylic esters are generally synthesized by transesterification reaction between a light alcohol (meth)acrylate (denoted light (meth)acrylate) and a heavy alcohol (corresponding $C_4$-$C_{12}$ alcohol).

This reaction is an equilibrated catalyzed reaction with generation of light alcohol, which it is necessary to remove during the reaction in order to shift the equilibrium in the direction of the production of the (meth)acrylic ester.

The secondary reactions during the synthesis produce impurities, generally byproducts with a high boiling point or with a boiling point close to the boiling point of the desired ester, which it is necessary to remove for the purpose of obtaining the (meth)acrylic ester with a high purity, satisfying the technical requirements related to its final use as monomer to manufacture polymers which can be used in numerous fields of application.

Furthermore, the upgradable products present in the reaction mixture, in particular the unreacted reactants and the catalyst, are as far as possible recycled within the process.

For these purposes, a separation/purification process, comprising a series of distillations, extractions and/or separations by settling, is generally carried out, which process is both relatively complex to carry out and expensive from an energy and capital cost viewpoint for an industrial plant.

Processes for the purification of (meth)acrylic esters have been widely described in the prior art.

Mention may be made, for example, of the document U.S. Pat. No. 7,268,251, in which the reaction effluent originating from a transesterification is treated by a process requiring the use of at least four distillation or rectification columns, including an evaporator for separating the catalyst. It turns out that the process described in the document U.S. Pat. No. 7,268,251 is complicated to carry out on the industrial scale, as a result of the optimization of the operating conditions of the sequence of the four distillation/rectification elements, in order to obtain a product of high purity and a satisfactory output. This process, which is very expensive in capital costs, additionally requires a large surface area for installation. It is illustrated with the manufacture of dimethylaminoethyl acrylate from dimethylaminoethanol and ethyl acrylate.

The document EP 960877, on behalf of the applicant company, illustrates another process for the manufacture of dimethylaminoethyl acrylate. This process consists of a removal of the catalyst and of the heavy products (tailing), followed by a removal of the light compounds (topping) and by a final rectification of a crude reaction mixture. This process thus exhibits the advantage of comprising only three distillation columns in the line for purification of the reaction mixture.

The document U.S. Pat. No. 7,294,240 B2 describes a process for the continuous manufacture of (meth)acrylic esters, in particular the manufacture of dimethylaminoethyl acrylate from dimethylaminoethanol and butyl acrylate, by combining a synthesis carried out in a reaction system comprising two reactors in series, in order to limit the secondary reactions, a column which makes it possible to separate the catalyst from the remainder of the reaction mixture and a sidestream distillation column which makes it possible to obtain a dimethylaminoethyl acrylate of high purity. The purification of the reaction mixture employs two distillation columns and the purified ester is drawn off as a sidestream from the second column.

The document WO 2013/110876 describes a purification process suitable in particular for 2-octyl acrylate, comprising a preliminary separation of the catalyst and the purification using two distillation columns in series or one sidestream distillation column. Furthermore, the proposal has been made to use a single sidestream distillation column in order to purifier, in a single stage, a $C_4$-$C_9$ alkyl acrylate reaction mixture, as described in the document WO 2014/096648 on behalf of the applicant company.

Generally, the processes of the prior art combine a first separation of the catalyst from the reaction medium, then a distillation of the reaction mixture devoid of catalyst using one or two distillation columns, in order to obtain a (meth)acrylic ester of high purity.

Simplified purification processes are provided by virtue of the development of divided wall distillation columns (known under the name DWC—Divided Wall Column). The technology is based on a distillation column comprising an internal separating wall which makes it possible to combine the operation of two columns conventionally in series in a single item of equipment.

By way of example, the patent application EP 2659943 describes a configuration of a divided wall column and its operation in a process for the production of 2-ethylhexyl acrylate of high purity. Although this column is complex to manufacture and to operate, it exhibits the advantage of reducing the equipment cost and the energy consumption of the purification process, in comparison with a conventional installation comprising two distillation columns. The question of the stabilization necessary for its satisfactory operation is not broached. The purification process described in this document makes no mention of problems related to the preliminary separation of the catalyst, the presence of which can cause retrogradation reactions in the divided wall column.

The patent application JP 2005-239564 also describes the use of a divided wall column in a process for the synthesis of (meth)acrylic esters, exemplified in the case of the synthesis of butyl methacrylate by transesterification reaction between methyl methacrylate and butanol. In this process, a mist eliminator is combined with the dividing wall column in order to prevent the entrainment of droplets of stabilizers in the sidestream withdrawal and to control the amount of stabilizers in the purified product. The divided wall column makes it possible to carry out the separation of the targeted ester with the heavy products and the lighter products. However, the purification process described in this document is applicable to the production of aminoalkyl (meth)acrylates and does not solve the question of the preliminary separation of the catalyst when the esters are sensitive to retrogradation reactions. In particular, the presence of the catalyst in the divided wall column risks bringing about cracking reactions resulting in the formation of compounds which contaminate the purified product drawn off as a sidestream.

The technology of divided wall columns in general is known and described, for example, by Asprion N. et al., "Dividing wall columns: Fundamentals and recent advances", Chemical Engineering and Processing, vol. 49 (2010), pages 139-146, or by Dejanovic I. et al., "Dividing wall column—A breakthrough towards sustainable distilling", Chemical Engineering and Processing, vol. 49 (2010), pages 559-580.

However, the different configurations described relate solely to the expected energy saving, and the state of the art in its entirety does not in the least suggest the type of configuration suitable for the purification of crude (meth) acrylic reaction mixtures resulting from a catalytic transesterification reaction.

A need still remains to improve the purification of "heavy" (meth)acrylic esters, such as, for example, dimethylaminoethyl acrylate or 2-octyl acrylate, in terms of separation/recycling of the catalyst and of energy balance of the overall purification process.

The objective of the present invention meets this need by providing a process for the recovery of a $C_4$-$C_{12}$ (meth) acrylic ester purified using a purification system comprising a divided wall column employed in a particular configuration, which makes it possible to avoid the risk of contamination of the finished ester produced by the retrogradation reactions in the presence of catalyst in the column.

The invention thus provides a technical/economic solution to the problem of the purification of a crude reaction mixture resulting from the transesterification reaction of a light (meth)acrylic acid ester by a $C_4$-$C_{12}$ alcohol, with a reduction in the capital and installation costs related to a decrease in the number of columns and of related items of equipment (pumps, exchangers, and the like), but also with a processing energy gain, while responding to the demand as regards purity of the ester produced.

SUMMARY OF THE INVENTION

A subject matter of the invention is a process for the recovery of a purified $C_4$-$C_{12}$ (meth)acrylic ester, from a crude reaction mixture obtained by transesterification of a light (meth)acrylic ester by the corresponding alcohol, said process being characterized in that it is carried out using a purification system comprising a divided wall column equipped with a separating wall creating separation zones in the column, the wall not being joined to the upper dome of the column in the top part and being joined to the bottom of the column in the bottom part, said divided wall column combined at the top with a single condenser and at the bottom with two boilers, comprising a common rectification section above the wall, a prefractionation section comprising the feeding of the column, a withdrawal section separated from the prefractionation section by the wall comprising the withdrawal of the purified ester, and characterized in that i) a gas stream is extracted at the top of the rectification section and recycled after condensation at least in part in the reactor, ii) a stream is withdrawn at the bottom of the prefractionation section and recycled at least in part in the reactor, iii) a stream is withdrawn at the bottom of the withdrawal section and recycled at least in part in the prefractionation section of the column, and iv) a stream of purified (meth) acrylic ester is drawn off as a sidestream from the withdrawal section at a point located above the bottom withdrawal of said withdrawal section.

According to the invention, the crude reaction mixture subjected to the process of recovery of the purified (meth) acrylic ester comprises at least a part, preferably all, of the catalyst employed for the transesterification reaction.

The process according to the invention is applied to the synthesis of alkyl (meth)acrylates, the alcohol used in the transesterification reaction being a primary or secondary aliphatic alcohol comprising a linear or branched alkyl chain comprising from 4 to 12 carbon atoms, preferably from 5 to 10 carbon atoms, and being able to be interrupted by one or more heteroatoms, such as N or O, preferably N.

According to one embodiment of the invention, the alcohol is a primary or secondary aliphatic alcohol, having a linear or branched alkyl chain comprising from 4 to 12 carbon atoms, preferably from 5 to 10 carbon atoms.

Mention may be made, as examples of alcohol, of 2-ethylhexanol, 2-octanol or 2-propylheptanol. Preferably, the alcohol is 2-octanol.

According to one embodiment of the invention, the alcohol is an aminoalcohol, in particular a dialkylaminoalcohol, of formula:

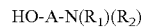

in which

A is a linear or branched $C_1$-$C_5$ alkylene radical, $R_1$ and $R_2$, which are identical to or different from each other, each represent a $C_1$-$C_4$ alkyl radical.

Mention may be made, as examples of alcohol, of N,N-dimethylaminoethanol (DMAE), N,N-diethylaminoethanol or N,N-dimethylaminopropanol.

Preferably, the alcohol is N,N-dimethylaminoethanol (DMAE), also denoted in the continuation of the account by dimethylaminoethanol.

Light (meth)acrylic ester is understood to mean a (meth) acrylate having a $C_1$ or $C_2$ alkyl chain, such as methyl (meth)acrylate or ethyl (meth)acrylate.

The term "(meth)acrylic" means acrylic or methacrylic; the term "(meth)acrylate" means acrylate or methacrylate.

Preferably, the light (meth)acrylic ester is methyl acrylate or ethyl acrylate, more preferably ethyl acrylate.

According to a preferred embodiment, the purified $C_4$-$C_{12}$ (meth)acrylic ester is a purified $C_4$-$C_{12}$ acrylate, more preferably 2-octyl acrylate or dimethylaminoethyl acrylate (DAMEA).

The recovery process according to the invention results in a $C_4$-$C_{12}$ (meth)acrylate with a purity at least equivalent to that obtained in a conventional installation comprising at least two separation columns, this being the case under operating conditions which minimize the thermal degradation of the heat-sensitive compounds, and under more economical energy conditions.

Another subject matter of the invention is the use of a purification system for recovering a purified $C_4$-$C_{12}$ (meth) acrylic ester, starting from a crude reaction mixture obtained by catalytic transesterification of a light (meth)acrylic ester by the corresponding alcohol, said system comprising a divided wall column equipped with a separating wall creating separation zones in the column, the wall not being joined to the upper dome of the column in the top part and being joined to the bottom of the column in the bottom part, said divided wall column combined at the top with a single condenser and at the bottom with two boilers, comprising a common rectification section above the wall, a prefractionation section comprising the feeding of the column with a mixture to be purified, a withdrawal section separated from the prefractionation section by the wall comprising the withdrawal of the purified product.

Another subject matter of the invention is a process for the production of a purified $C_4$-$C_{12}$ (meth)acrylic ester, by transesterification of a light (meth)acrylic ester with the corresponding alcohol, characterized in that the crude reaction mixture is subjected to the recovery process using the purification system as defined above.

Thus, the invention makes it possible to achieve the desired specifications in terms of purity of the (meth)acrylic esters under economic conditions.

BRIEF DESCRIPTION OF THE FIGURE

The FIGURE represents the configuration of a purification system comprising a divided wall column which can be used in the process according to the invention.

DETAILED ACCOUNT OF THE INVENTION

The invention is now described in greater detail and in a nonlimiting manner in the description which follows.

For the sake of simplicity of the continuation of the account, and in a nonlimiting manner, the process of the invention is described with reference to the production of dimethylaminoethyl acrylate (DAMEA) obtained by transesterification starting from ethyl acrylate (EA) and dimethylaminoethanol (DMAE).

In the transesterification reactor, the light compounds present in the reaction medium are generally the residual reactants—ethyl acrylate and dimethylaminoethanol in this particular case.

A cyclization reaction can result in the formation of 1,4-dimethylpiperazine (DMPPZ), the boiling point of which is close to that of dimethylaminoethanol. This byproduct will thus be extracted at the same time as the residual alcohol.

As secondary reactions resulting in the formation of heavy byproducts during the synthesis of (meth)acrylic esters, there exists in particular a Michael addition reaction of a molecule containing a labile hydrogen atom (such as an alcohol) to the double bond of a (meth)acrylic compound (such as the light (meth)acrylate or the (meth)acrylic ester formed). Cyclization reactions can also take place.

In the particular case of the manufacture of DAMEA from EA and DMAE, the still unreacted DMAE alcohol or the ethanol released add to the double bond of the DAMEA already formed or of the unreacted EA, to form heavy Michael addition byproducts [DMAE+DAMEA] or [DMAE+EA].

One characteristic of these byproducts is that their boiling point is above the boiling points of the products employed in the reaction and/or of the DAMEA desired. This is why these combined byproducts are subsequently known as heavy byproducts.

In the particular case of the synthesis of DAMEA, the heavy byproducts comprise Michael adducts, in particular ethyl ethoxypropionate (EEP), amiethyl ethoxypropionate (AEP), amiethyl amietoxypropionate (AAP) and ethyl amietoxypropionate (EAP), and various other heavy compounds.

The objective of the process according to the invention is to recover the (meth)acrylic ester with a purity of greater than 99.5%, preferably of greater than 99.8%, from the reaction mixture comprising light byproducts (volatile compounds or light compounds), heavy byproducts (heavy compounds or least volatile compounds), and also the transesterification catalyst, and the polymerization inhibitors generally added to the transesterification reactor. This can be carried out with a purification system comprising a separating wall column combined with a condenser at the top and two boilers at the bottom, as represented in the FIGURE.

With reference to the FIGURE, the divided wall column used in the process according to the invention comprises a partial vertical wall (or partition) P placed inside the column, thus defining three distinct zones: an upper zone, denoted rectification section, a central zone comprising two zones on either side of the partition and extending as far as the bottom of the column.

According to one embodiment, the wall can be in part diagonal. The wall can be flat or cylindrical, so that the spaces separated by the wall can be positioned in concentric form.

The wall as installed does not necessarily separate the central zone into two equal zones; this is because it can be advantageous in some embodiments to have unequal zones in order to minimize the loss of head or the tendency to choking, according to the nature or the intensity of the streams circulating in the column.

The height of the wall represents from 30% to 70% of the height of the column.

The central zone consists of two zones on either side of the wall, one of which represents a "prefractionation" section and the other a withdrawal section for the pure product.

For the sake of simplicity in the continuation of the account of the invention, "prefractionation section" is understood to mean the section of the separating wall column which is fed by the stream of (meth)acrylic ester to be purified, the feeding only taking place on a single side of the wall, and "withdrawal section" is understood to mean the section of the column on the other side of the separating wall, from where the stream of purified (meth)acrylic ester is extracted as a sidestream.

The prefractionation section, combined with a boiler B1, comprises the feeding F of the column, thus separating a section S1 above the feeding and a section S2 below the feeding. The prefractionation section has the effect of concentrating the most volatile products, known as light compounds, at the top of the column and of concentrating the least volatile products, known as heavy compounds, at the bottom of the column. It is in particular in this prefractionation section, combined with the boiler B1, that the catalyst, a large part of the polymerization inhibitors and also the heavy impurities are found at the bottom of this section. This prefractionation bottom product can be upgraded by recycling all or part of the latter in the transesterification reactor.

According to one embodiment, the feeding is located in the lower half of the prefractionation section, preferably in the lower third, for example under the final plate.

The withdrawal section comprises a side outlet in order to withdraw the purified ester S, the side outlet dividing the withdrawal section into two sections S4 and S5. The withdrawal of the purified ester can be carried out in the form of a liquid stream or of a gas stream; preferably, a gas stream is withdrawn. In this section, the light compounds and also the ester are sent to the top of the column and heavy compounds are sent to the bottom of the column. A bottom stream essentially comprising heavy compounds and polymerization inhibitors and a small amount of ester produced is withdrawn from the withdrawal section combined with a boiler B2 and is advantageously recycled, at least in part, in the prefractionation section, preferably at the feeding F, or at a point located above or below the feeding. The recycling of the bottom product from the withdrawal section makes it possible to minimize the losses of (meth)acrylic ester.

According to one embodiment, the sidestream withdrawal point is located in the lower half of the withdrawal section, preferably in the lower quarter.

A common zone, known as rectification section S3, is found above the wall at the top of the dividing wall column, which section makes it possible to separate the light compounds, which are extracted, then condensed, at least in part, in the condenser C combined with the column. This condensed product is returned, in part, as reflux to the section S3, the other part advantageously being sent, at least in part, to the inlet of the reactor, since it consists mainly of unreacted reactants and a small amount of ester formed.

A liquid reflux at the column top can thus be provided. Above the wall, the liquid is recovered and separated on either side of the wall toward the sections S1 and S4. The fraction by weight of liquid returning toward the section S1 is generally between 20% and 50%.

A certain number of parameters characterize the design and the operation of the divided wall column. They mainly concern the number of theoretical stages in each section of the divided wall column, in particular the numbers N1, N2, N3, N4 and N5 corresponding respectively to the number of stages of each of the sections S1 to S5 described above, the reflux ratio of the column, the ratio of liquid stream originating from the rectification section on each side of the wall, the ratio of gas stream originating from the reboiling section on each side of the partition, the positioning of the feeding point F or of the point for sidestream withdrawal S of the pure product.

These different parameters can be determined from methods known to a person skilled in the art, so that the (meth)acrylic ester is produced with a purity meeting the desired specifications.

The divided wall column and the internal parts present are chosen in order to obtain the number of necessary theoretical stages in each section. It will be possible to use, as internal parts, plates, stacked packing, such as structured packing, or random packing.

According to one embodiment, the number of theoretical stages of the prefractionation section S1+S2 is between 1 and 20, and the feeding of the column is preferably placed in the final lower third approximately of this section.

According to one embodiment, the number of theoretical stages of the withdrawal section S4+S5 is between 1 and 15, and the point for withdrawal of the purified ester is preferably placed in the final lower quarter approximately of this section.

According to one embodiment, the number of theoretical stages of the rectification section S3 is between 1 and 15.

The column can operate under vacuum, in order to minimize the thermal exposure of the heat-sensitive compounds within the column. Advantageously, the column operates under a vacuum ranging from 10 to 100 mm of Hg.

Advantageously, the operating temperature is between 50° C. and 150° C.

The internal parts used for the column can be valve plates or perforated plates having a weir, or structured packing.

Apart from the operating conditions suitable for the transesterification reaction minimizing the formation of the heavy compounds and optimizing the yield of the reaction, it is necessary to introduce polymerization inhibitors (also known as stabilizers) not only during the reaction but also during the purification of the crude reaction mixture exiting from the esterification reactor.

The inventors have discovered that the stabilization of the purification system combining a divided wall column is more advantageous than the stabilization of a conventional plant comprising two columns in series. This is because the polymerization inhibitor used to stabilize the desired ester can be introduced into the purification system as single polymerization inhibitor; this results in the stabilization being simpler and consistent. Alternatively, a less expensive polymerization inhibitor can be used to stabilize the divided wall column, and the purified ester is subsequently stabilized with another compound more suitable for stabilizing the finished product for the purpose of its subsequent storage and use. In this case, the cost related to the polymerization inhibitors can be greatly reduced.

Mention may be made, as polymerization inhibitors which can be used, for example, of phenothiazine (PTZ), hydroquinone (HQ), hydroquinone monomethyl ether (HQME), di(tert-butyl)-para-cresol (BHT), para-phenylenediamine, TEMPO (2,2,6,6-tetramethyl-1-piperidinyloxy), di(tert-butyl)catechol, or TEMPO derivatives, such as OH-TEMPO, alone or their mixtures in all proportions.

According to one embodiment, the purification system is stabilized using a single polymerization inhibitor, preferably injected at the top condenser, the purified (meth)acrylic ester being withdrawn as a sidestream from the divided wall column in the form of a stabilized liquid or gas stream.

According to this embodiment, it is preferable to use hydroquinone monomethyl ether as stabilizer.

According to one embodiment, the purification system is stabilized using a first polymerization inhibitor, preferably injected at the top condenser, the purified (meth)acrylic ester being withdrawn as a sidestream from the divided wall column in the form of a gas stream which, after condensation, is subsequently stabilized with a different polymerization inhibitor from the first inhibitor. According to this embodiment, it is possible to use a first inhibitor which is markedly cheaper and to be freed from its presence in the purified product by carrying out a gas-phase withdrawal, the first polymerization inhibitor remaining in the stream of heavy byproducts separated at the column bottom. Phenothiazine or OH-TEMPO may be suitable as first polymerization inhibitor as they also make it possible to stabilize all the organic streams. The purified product withdrawn as a sidestream is then stabilized, after condensation, according to conventional practice, for example using hydroquinone methyl ether.

Advantageously, from 100 to 5000 ppm of polymerization inhibitor are introduced during the purification of the reaction mixture into the purification system according to the process of the invention.

In order to render the inhibitors more effective, it is possible to inject, at the column bottom, oxygen, air or "depleted" air, for example comprising 7% $O_2$. Preferably, the amount of oxygen injected corresponds to a content of 0.2 vol % to 0.5 vol %, with respect to the amount of organic vapor in the column.

Purified (meth)acrylic ester is understood to mean a product having a content of (meth)acrylic ester >99.5% by weight, preferably >99.8% by weight, and generally a content of heavy impurities of less than 1500 ppm, advantageously of less than 1200 ppm.

Another subject matter of the invention is a process for the production of a purified $C_4$-$C_{12}$ (meth)acrylic ester by transesterification, characterized in that the crude reaction mixture is subjected to the recovery process using a purification system as defined above.

The conditions of the transesterification reaction are those known to a person skilled in the art and can be implemented according to a process of continuous, semicontinuous or batch type.

The invention thus provides a process for the production of a $C_4$-$C_{12}$(meth)acrylic ester in a compact plant, the capital and operating cost of which is reduced, and providing a product of high purity with an optimized yield.

In comparison with the processes of the prior art, it is possible to reduce by more than 10% the energy consumption for carrying out the purification process according to the invention. In addition, the content of impurities which are difficult to separate as a result of their similar boiling point to that of the desired ester is found to be minimized in the purified product obtained according to the process according to the invention.

The examples below illustrate the present invention without, however, limiting the scope thereof.

EXPERIMENTAL PART

In the examples, the percentages are shown by weight, unless otherwise indicated, and the following abbreviations were used:
EA: Ethyl acrylate
AAP: amiethyl amietoxypropionate
AEP: amiethyl ethoxypropionate
EEP: ethyl ethoxypropionate
DAMEA: dimethylaminoethyl acrylate
PTZ: phenothiazine
DMAE: dimethylaminoethanol
HQME: hydroquinone methyl ether
Catalyst: expressed in the form of ethyl titanate

EXAMPLE 1 (COMPARATIVE)

Purification Using 3 Distillation Columns in Series

A crude DAMEA reaction mixture resulting from the synthesis by transesterification of ethyl acrylate and dimethylaminoethanol was subjected to a purification treatment using three distillation columns in series.

The first column comprises an equivalent, in theoretical stages, of 9 and it is combined at the bottom with a boiler and at the top with a condenser in which an organic phase is recycled partly in the column in order to provide the column with a reflux. The column is stabilized by injection of PTZ at the top condenser. The energy supplied by the boiler is 0.74 MW.

The second column comprises an equivalent, in theoretical stages, of 14 and it is combined at the bottom with a boiler and at the top with a condenser. It is fed by the bottom stream from the first column, which comprises the DAMEA, and also the light products (EA, DMAE) and heavy byproducts, such as the Michael adducts. The second column is stabilized by injection of PTZ at the top condenser. The energy supplied by the boiler is 0.61 MW.

The third column comprises an equivalent, in theoretical stages, of 4 and it is combined at the bottom with a boiler and at the top with a condenser. It is fed by the bottom stream from the second column, which comprises the DAMEA, heavy byproducts, such as the Michael adducts, and the stabilizers. The third column is stabilized by injection of HQME at the top condenser. The energy supplied by the boiler is 0.36 MW. The purified DAMEA distils at the top of the third column.

The feed of the first column has the following composition by weight and characteristics:
DAMEA: 48%—EA: 23%—DMAE: 14%
AAP: 1%—AEP: 0.2%—EEP: 0.04%—other heavy products: 164 ppm, catalyst: 1.5%
Total stream: 6780 kg/h—temperature: 110° C.—pressure: 0.891 bar An ASPEN simulation using a thermodynamic model was carried out and provides the following composition by weight for the purified product distilled at the top of the third column.
DAMEA: 99.8%—DMAE: <1 ppm
AAP traces—AEP: 214 ppm—EEP: 889 ppm—heavy products, including AEP: 729 ppm
Total stream: 2870 kg/h—temperature: 35° C.—pressure: 0.05 bar.

In this configuration, the DAMEA with a purity of greater than 99.8% is recovered with a yield of the order of 88%, with respect to the feed stream. The overall energy consumption is 1.7 MW. The sum of the heavy impurities (EEP, AEP, other heavy products) amounts to 1618 ppm.

Example 2 (Comparative): Purification Using 2 Distillation Columns in Series and Sidestream Withdrawal of the Purified Product A crude DAMEA reaction mixture resulting from the synthesis by transesterification of ethyl acrylate and dimethylaminoethanol was subjected to a purification treatment using two distillation columns in series.

The first column comprises an equivalent, in theoretical stages, of 9 and it is combined at the bottom with a boiler and at the top with a condenser in which an organic phase is recycled partly in the column in order to provide the column with a reflux. The column is stabilized by injection of PTZ at the top condenser. The energy supplied by the boiler is 0.74 MW.

The second column comprises an equivalent, in theoretical stages, of 16 and it is combined at the bottom with a boiler and at the top with a condenser. It is fed by the bottom stream from the first column, which comprises the DAMEA, and also the light products (EA, DMAE) and heavy byproducts, such as the Michael adducts. The second column is stabilized by injection of HQME at the top condenser. The energy supplied by the boiler is 0.8 MW. This second column is a sidestream withdrawal column and the purified DAMEA is withdrawn in the lower third of the column.

The feed of the first column has the following composition by weight and characteristics:
DAMEA: 48%—EA: 23%—DMAE: 14%
AAP: 1%-AEP: 0.2%—EEP: 0.04%—other heavy products: 164 ppm, catalyst: 1.5%
Total stream: 6780 kg/h—temperature: 110° C.—pressure: 0.891 bar An ASPEN simulation using a thermodynamic model was carried out and provides the following composition by weight for the purified product obtained by sidestream withdrawal.
DAMEA: 99.8%—DMAE: <1 ppm
AAP traces—AEP: 510 ppm—EEP: 936 ppm—heavy products, including AEP: 534 ppm Total stream: 2870 kg/h—temperature: 120° C.—pressure: 0.188 bar In this configuration, the DAMEA is recovered with a yield of the order of 88%, with respect to the feed stream, and the DAMEA has a purity of greater than 99.8%. The overall energy consumption is 1.54 MW. The sum of the heavy impurities (EEP, AEP, other heavy products) amounts to 1470 ppm.

Example 3 (According to the Invention)

An ASPEN simulation using a thermodynamic model was carried out on the crude DAMEA reaction mixture, as described in examples 1 and 2, but subjected to a purification using the purification system as represented in the FIGURE.

In this example, the divided wall column is stabilized at the top condenser with PTZ and the DAMEA withdrawn as a sidestream in the gas phase is stabilized with HQME.

In this configuration, the number of plates of the different sections is as follows:

N1: 8—N2: 6—N3: 5—N4: 10—N5: 1.

The energy supplied by the boiler is 1.4 MW.

The purified product withdrawn as a sidestream has the following composition by weight:

DAMEA: 99.8%—DMAE: traces

AAP traces—AEP: 237 ppm—EEP: 919 ppm—heavy products, including AEP: 254 pm

Total stream: 2870 kg/h—temperature: 110° C.—pressure: 0.118 bar

In this configuration, the DAMEA is recovered with a yield of the order of 88%, with respect to the feed stream, and the DAMEA has a purity of greater than 99.8%.

The overall energy consumption is 1.4 MW. The sum of the heavy impurities (EEP, AEP, other heavy products) amounts to 1173 ppm.

In comparison with the purification process of the prior art using 2 or 3 distillation columns, the heat necessary to purify the reaction stream is reduced by the order of 18% (scheme having 3 columns) or of 10% (scheme having 2 columns).

The content of heavy impurities also significantly decreases, of order of 20% to 30%.

Example 4: Degradation of the Bottom Product During the Distillation

The aim of this example is to show the importance of the positioning of the separating wall in the divided wall column for the quality of the product obtained in sidestream withdrawal, in particular the need to have a wall separating the bottom part of the column.

We used a laboratory assembly composed of a stirred reactor, of a distillation column and of an oil bath which makes it possible to heat the product to the desired temperature.

A mixture having a composition close to the composition expected at the bottom of the distillation column at the boiler B1 was introduced into the reactor and subjected to a temperature of 140° C. at P atm for 3 hours.

The distillate collected at the top of the distillation column and the distillation bottom product were subsequently analyzed.

The amounts by weight of the light products distilled, in comparison with the amounts present in the mixture introduced into the reactor, are presented in the table below.

|        | Feed | Distillate | Comments  |
|--------|------|------------|-----------|
| EtOH, g | 0    | 0.086      | Formation |
| EA, g   | 0    | 0.145      | Formation |
| DMAE, g | 0    | 10.87      | Formation |
| EEP, g  | 0    | 0.706      | Formation |

This test shows that the bottom product of the distillation column, as a result of the presence of catalyst, changes and forms light compounds when it is maintained at temperature.

According to the invention, a separating wall extending as far as the bottom of the column makes it possible to prevent these light products from contaminating the sidestream withdrawal.

The invention claimed is:

1. A process for the recovery of a purified $C_4$-$C_{12}$ (meth) acrylic ester, from a crude reaction mixture obtained by transesterification of a light (meth)acrylic ester by the corresponding alcohol, said crude reaction mixture comprising a transesterification catalyst, wherein the corresponding alcohol is a primary or secondary aliphatic alcohol, having a linear or branched alkyl chain comprising from 4 to 12 carbon atoms, said process being carried out using a purification system comprising a divided wall column equipped with a separating wall creating separation zones in the column, the wall not being joined to the upper dome of the column in the top part and being joined to the bottom of the column in the bottom part, said divided wall column combined at the top with a single condenser and at the bottom with two boilers, comprising a common rectification section above the wall, a prefractionation section comprising the feeding of the column, a withdrawal section separated from the prefractionation section by the wall comprising the withdrawal of the purified ester, and said process comprising the steps of i) extracting a gas stream at the top of the rectification section and recycling after condensation at least in part in the purification column, ii) withdrawing a stream at the bottom of the prefractionation section and recycling at least in part in the purification column, iii) withdrawing a stream at the bottom of the withdrawal section and recycling at least in part in the prefractionation section of the column, and iv) drawing off a stream of purified (meth)acrylic ester as a sidestream from the withdrawal section at a point located above the bottom withdrawal of said withdrawal section.

2. The process as claimed in claim 1, wherein the alcohol is 2-ethylhexanol, 2-octanol or 2-propylheptanol.

3. The process as claimed in claim 1 wherein the alcohol is a dialkylaminoalcohol, of a formula:

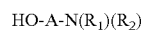

HO-A-N($R_1$)($R_2$)

in which

A is a linear or branched $C_1$-$C_5$ alkylene radical, and $R_1$ and $R_2$, which are identical to or different from each other, each representing a $C_1$-$C_4$ alkyl radical.

4. The process as claimed in claim 3, wherein the alcohol is N,N-dimethylaminoethanol, N,N-diethylaminoethanol or N,N-dimethylaminopropanol.

5. The process as claimed in claim 1 wherein the light (meth)acrylic ester is methyl (meth)acrylate or ethyl (meth)acrylate.

6. The process as claimed in claim 1 wherein the number of theoretical stages of the rectification section is between 1 and 15.

7. The process as claimed in claim 1 wherein the number of theoretical stages of the prefractionation section is between 1 and 20.

8. The process as claimed in claim 1 wherein the number of theoretical stages of the withdrawal section is between 1 and 15.

9. The process as claimed in claim 1 wherein the purification system is stabilized using a single polymerization inhibitor, the purified (meth)acrylic ester being withdrawn as a sidestream from the divided wall column in the form of a stabilized liquid or gas stream.

10. The process as claimed in claim 1 wherein the purification system is stabilized using a first polymerization inhibitor, the purified (meth)acrylic ester being withdrawn as a sidestream from the divided wall column in the form of a gas stream which, after condensation, is subsequently stabilized with a different polymerization inhibitor from the first inhibitor.

11. The process as claimed in claim 1 wherein the purified $C_4$-$C_{12}$ (meth)acrylic ester is dimethylaminoethyl acrylate or 2-octyl acrylate.

12. A process for the production of a purified $C_4$-$C_{12}$ (meth)acrylic ester, by transesterification of a light (meth)acrylic ester with the corresponding alcohol, wherein the crude reaction mixture is subjected to the recovery process as claimed in claim 1.

* * * * *